United States Patent [19]

Pena et al.

[11] Patent Number: 5,599,674
[45] Date of Patent: Feb. 4, 1997

[54] FINGERPRINTING USING SINGLE SPECIFIC PRIMERS IN LOW STRINGENCY POLYMERASE CHAIN REACTION CONDITIONS

[75] Inventors: Sergio D. J. Pena, Gene Av. Afonso Pena 3111/9, 30130-909 Belo Horizonte, MG; Andrew J. G. Simpson, Belo Horizonte, both of Brazil

[73] Assignee: Sergio D. J. Pena, Belo Horizonte, Brazil

[21] Appl. No.: 406,635

[22] Filed: Mar. 20, 1995

Related U.S. Application Data

[63] Continuation of Ser. No. 100,738, Jul. 29, 1993, abandoned.
[51] Int. Cl.$^6$ .............................. C12Q 1/68; C12P 19/34; C07H 21/04
[52] U.S. Cl. .................. 435/6; 435/5; 435/91.2; 422/68.1; 536/23.1
[58] Field of Search .................. 435/6, 91.2, 5; 422/68.1, 70; 536/23.1

[56] References Cited

U.S. PATENT DOCUMENTS

| 4,683,202 | 7/1987 | Mullis | 435/91.2 |
| 5,437,975 | 8/1995 | McClelland et al. | 435/6 |

OTHER PUBLICATIONS

Reinach, F. C. et al.; Site–directed Mutagenesis of the Regulatory Light–chain $Ca^{2+}/Mg^{2+}$ Binding Site and its Role in Hybrid Myosins; *Nature* (1986) 322:80;.
Saiki, R. K. et al.; Genetic Analysis of Amplified DNA with Immobilized sequence–specific oligonucleotide probes; *Proc Natl Acad Sci USA* (1989) 86:6230;.
Orita, M. et al.; Rapid and Sensitive Detection of Point Mutations and DNA Polymorphisms Using the Polymerase Chain Reaction; *Genomics* (1989) 5:874.
Sheffield, B. C. et al.; Attachment of a 40–base–pair G + C–rich sequence (GC–clamp) to Genomic DNA Fragments by the Polymerase Chain Reaction Results in Improved Detection of Single–base Changes; *Proc Natl Acad Sci USA* (1989) 86:232;.
Stoneking, M. et al.; Population of Human mtDNA Control Region Sequences Detected by Enzymatic Amplification and Sequence–specific Oligonucleotide Probes; *Am J Hum Genet* (1991) 48:370;.
Dias Neto, E. et al.; Sex Determination by Low Stringency CPR (LS–PCR); *Nucleic Acids Res* (1993) 21:763–764;.
Welsch, J. et al.; Fingerprinting genomes usign PCR with arbitrary primers; *Nucleic Acids Res* (1990) 18:7213–7218.
Versalovic et al., *Nuc. Ac. Res.* 19(24), 6823–6831 (1991).
Ledbetter et al., *Genomics* 6, 475–481 (1990).
Dias Neto et al., *Mol. Biochem. Parasit.* 57, 83–88 (1993).
Nelson et al., *PNAS* 86, 6686–6690 (1989).
Williams et al., *Nuc. Ac. Res.* 18(22), 6531–6535 (1990).
Wu et al., *DNA Cell Biol.* 10(3), 233–238 (1991).

*Primary Examiner*—Kenneth R. Horlick
*Attorney, Agent, or Firm*— Morrison & Foerster LLP

[57] ABSTRACT

A straightforward method to characterize a nucleotide sequence of a defined DNA region is described. A purified segment representing the defined region is subjected to repeated cycles of amplification (PCR) using a single primer complementary to a portion of the segment under conditions of low stringency and high polymerase and primer concentrations. PCR under these conditions results in a mixture of amplified DNA molecules the composition of which is characteristic of the DNA segment assessed. Determination of the composition of the mixture can be obtained by subjecting the mixture to standard chromatographic or electrophoretic techniques to obtain a pattern of fragments which represents a "signature" of the nucleotide sequence.

11 Claims, 6 Drawing Sheets

```
      140                                        180
WT    CGACCAGAACCGTGACGGGTTCATTGACAAGGAGGATCTGCAT
R4G   -----------G------------------------------
D12A  --------------------------------C---------
D12E  -------------------------------------G----
```

FINGERPRINTING USING SINGLE SPECIFIC PRIMERS IN LOW STRINGENCY POLYMERASE CHAIN REACTION CONDITIONS

This application is a continuation of application Ser. No. 08/100,738, filed 29 July 1993, abandoned.

TECHNICAL FIELD

The invention relates to the field of genetic analysis. More specifically, the invention concerns characterization of the nucleotide sequence of a purified defined region of DNA by conducting a PCR reaction under conditions of low stringency using a single specific primer.

BACKGROUND ART

In the past several years, the development of techniques capable of detecting DNA sequence variation has aroused a great deal of interest. Major applications include the study of genetic disease, cancer, and identity testing. While DNA sequencing is clearly the most sensitive and informative method, it is too cumbersome for routine use in searching for mutations, especially when the DNA segment of interest is large.

For detection of single-base mutations, alternatives to sequencing consist either of techniques dependent on prior knowledge of the exact base alterations sought, for instance techniques involving allele-specific hybridization (Reinach F. C. et al. *Nature* (1986) 322:80; Saiki, R. K. et al. *Proc Natl Acad Sci USA* (1989) 86:6230) or shotgun strategies that ideally would detect any change, for example, SSCP (Orita, M. et al. *Genomics* (1989) 5:874 and DGGE (Sheffield, B. C. et al. *Proc Natl Acad Sci USA* (1989) 86:232). Techniques relying on prior knowledge of the base alterations become awkward when sequence differences caused by a variable number of mutations are studied (Stoneking, M. et al. *Am J Hum Genet* (1991) 48:370). Shotgun strategies can only be applied to small DNA fragments and do not identify the number of modifications or their sites.

The present invention provides a new technique, called low stringency single-specific primer PCR (LSSP-PCR) that, when applied to gene-size DNA fragments, at least up to 1 kb, translates the underlying DNA sequence into a unique multiband "gene signature". Changes as small as single-base mutations significantly alter the signature that is diagnostic of the specific alteration.

Other techniques involving low stringency or random priming have also been disclosed. Dias Neto, E. et al. *Nucleic Acids Res* (1993) 21:763–764, describe a technique for sex determination by low stringency PCR. This technique utilizes conventional 2-primer PCR but with performance of the reaction under low stringency. When conducted in this way, the reaction mixture yields a pattern rather than a single amplified band. Low stringency conditions are also employed in the performance of random amplified polymorphic DNA (RAPD) as described by Welsch, J. et al. *Nucleic Acids Res* (1990) 18:7213–7218.

DISCLOSURE OF THE INVENTION

The invention provides a convenient and readily interpretable assay method for reproducibly obtaining a signature characteristic of a defined region of DNA. The defined region can, if desired, be prepared by amplification using standard PCR techniques or by cloning and ideally should be purified for application of the invention technique. The PCR reaction of the invention, designated herein low stringency single specific primer-PCR or LSSP-PCR, is conducted using only a single primer which hybridizes specifically to a portion of the defined DNA region (usually at its extremity) and which hybridizes nonspecifically under the low stringency conditions of the assay to multiple sites within the remainder of the defined region. Conduct of repeated polymerization cycles, particularly using high levels of Taq polymerase and primer, results in reproducible mixtures of amplified fragments which produce patterns that can be determined visually after subjecting the amplification mixture to standard separation techniques. The method is useful in identifying familial relationships, diagnosis of various diseases characterized by mutations in the gene, and in a variety of other applications.

Accordingly, in one aspect, the invention is directed to a method to characterize the nucleotide sequence of a defined, purified DNA segment which method comprises subjecting the segment to multiple cycles of replication in the presence of a single primer. The single primer is specifically complementary to a portion of the segment, preferably at its extremity, but binds nonspecifically to other portions under the low stringency conditions of the amplification. The replication is conducted with high levels of primer and Taq polymerase. The PCR reaction results in a mixture of amplified DNA molecules, the composition of which is characteristic of the DNA region assayed. The composition of the mixture is then determined using standard separation techniques or other methods of assessment known in the art to obtain a "signature" of the sequence.

In other aspects, the invention is directed to the resulting signatures, and to methods to apply the LSSP-PCR method to various practical situations.

In still an additional aspect, the invention relates to a method to provide a desired multiplicity of purified defined DNA segments which can be collectively subjected to the LSSP-PCR technique of the invention which method comprises subjecting each desired region of DNA to repeated cycles of replication using conventional PCR with the modification of one primer employed in this PCR so as to contain a "tail" DNA sequence, wherein said tail is common to one of the primers in all amplification reactions.

BRIEF DESCRIPTION OF THE DRAWINGS

FIGS. 4A and 4B show fingerprints of D-loop mitochondrial DNA derived from 3 members of a family in two different formats.

MODES OF CARRYING OUT THE INVENTION

The invention provides a convenient method to characterize the nucleotide sequence of any defined purified DNA segment. The resulting "signature" may further serve to characterize a subject from which the defined segment derives. The defined segment can be obtained from genomic or cDNA and can be defined using any known method, such as cleavage with restriction enzymes followed by size separation, retrieval of pre-cut inserts from available plasmids, and, most preferably, by using preliminary polymerase chain reaction (PCR) amplification of the defined region. The defined region is then purified using standard techniques such as gel electrophoresis and subjected to the invention method which can detect differences at least as minor as a single base pair mutation in an approximately 600 bp region.

Briefly, the invention method requires a defined and purified DNA segment to obtain a reliable signature. A defined region of DNA is recovered and purified and then subjected to repeated cycles of replication in a manner analogous to that practiced in PCR, except that one exactly complementary primer is used rather than two. Preferably the perfectly complementary primer is complementary to a portion of the defined DNA region at one of its extremities. The primer is employed under conditions of low stringency. The cycles of replication are comprised of a denaturing phase at high temperature and an annealing phase where the primers reassociate with the region to be amplified and polymerization catalyzed by Taq polymerase takes place. The stringency of the polymerization reaction is in general determined by its temperature. Low stringency conditions are characterized by low temperatures on the order of 25° C.–40° C. Elevation of the magnesium ion concentration also lowers stringency; however, regulation of the temperature of the polymerization phase of the replication cycle is preferred. Other conditions such as the concentration of the buffer, pH, ionic strength and the like are standard. However, the concentration of Taq polymerase and the primer are higher than commonly used, as is further described below. Under these conditions, while the primer clearly binds to the portion of the defined DNA region to which it is an exact complement, it can also bind, although less tightly, to various other portions of the defined fragment for which it is more or less a match.

While not wishing to be bound by a particular theory, it is believed that the extent of amplification based on a particular association of the primer with a mismatched portion of the fragment is governed by the balance of the rate of primer dissociation and the rate at which DNA polymerase extends the primer until a stable duplex is formed. See Wu, D. Y., et al. *DNA Cell Biol* (1991) 10:233–238.

The conditions for LSSP-PCR encompass not only a low stringency effected by a low temperature of annealing, but also exceptionally high concentrations of primer and Taq polymerase. Typically, primer concentrations are used in the range of 2–10 μM as compared to the usual range of 0.1–1 μM. It is also advantageous to use elevated concentrations of Taq polymerase, of the order of 60–200 units/ml. The remainder of the conditions under which PCR is conducted are standard. As long as identical conditions are maintained among determinations the results are reproducible.

The PCR reaction is conducted using any desired number of repetitions; 30–40 cycles is typical. The temperature is varied within a cycle; a particularly preferred protocol involves a cycle of several minutes in which the first ¼ to ⅓ of the cycle is conducted at a high temperature to denature the duplex and the remainder at a low temperature for hybridization of primer and polymerization.

The defined purified segment of DNA is thus contacted with the primer of a suitable number of nucleotides, typically 10–25, more commonly 15–20, which is a match for one portion of the primer. The reaction is conducted under standard buffer and salt conditions at a pH of about 7–10 in the presence of magnesium ion and Taq polymerase in a concentration range of 60–200 u/ml. A typical cycle lasts for 2–4 minutes and the temperature for at least a portion of the cycle is low, in the range of 30° C. Not all cycles in the protocol need be identical.

After accomplishing the requisite number of cycles, a mixture of DNA fragments which have been amplified based on the position and duration of binding of the primer to mismatched sites is obtained. The composition of the mixture is inherently characteristic of the nucleotide defined sequence of the DNA region.

The composition of the mixture must be analyzed in order to yield the requisite signature characterizing the sequence. Any art-recognized method of analysis may be used; at present, the most straightforward methods of analysis involve chromatographic or electrophoretic separation of the individual component fragments contained in the mixture. Typically, the components will vary both in size and in relative amount. The size distribution pattern is the more readily recognizable and reproducible.

Thus, typically, the mixture may be subjected to gel electrophoresis under conditions wherein the individual components are separated. The bands on the developed gel or other chromatographic support are then visualized using standard known techniques such as silver stain (see Santos, F. R. et al. *Hum Genet* (1993) 90:655–656). Other techniques for detection are those commonly used such as employing radioactively labeled nucleotides in the polymerization reaction to obtain autoradiograms or the use of fluorescent tags. A variety of detecting reagents, including antibodies or fragments which bind DNA generically is known. The pattern obtained on the gel can then be readily visualized and compared to other patterns.

As shown in Example 5 hereinbelow, the size of the purified defined DNA segment subjected to the LSSP-PCR technique of the invention does not affect the general nature of the pattern or signature obtained provided the length of the fragment is of the order of about 550 bp or greater. Extensions of the segment at the end distal to the portion which binds specifically to primer to a total length of over 1000 bp does not significantly alter the pattern. Similarly, extension at the end of the segment proximal to the portion binding specifically to primer does not seem to alter the pattern. Two conclusions follow from these results. First, the portion which binds specifically to primer, while preferably at the extremity of the segment to be subjected to the technique does not have to be precisely so located. Second, it may be advantageous when the segment to be tested is more than about 550 bp to utilize more than one LSSP-PCR determination, for example, conducting one such determination using a primer complementary to a portion at one extremity of the segment and a second determination using a primer complementary to a portion near the other extremity. This enhances the sensitivity of the determination and permits confirmation of identity or nonidentity of signatures from test samples.

In a modification of the method of the invention, initial performance of the traditional PCR reaction to provide the purified segment of DNA may employ, as at least one of the two primers, a primer having a sequence specific portion and a "tail". The "tail" extends the primer in the direction opposite to that from which extension of the primer will occur. The resulting amplified segments of DNA will carry the additional tail, which tail may incorporate desirable features that permit further manipulation.

In one application of this feature, multiple segments of DNA can be obtained in the initial sample which can then be subjected to the LSSP-PCR of the invention. The signature obtained from the sample will be unique to that particular combination of DNA segments. An application of this approach in assessing genomic sequences for mutations in the exons is described in further detail below. Another feature that may be incorporated into the tail is a restriction enzyme site which can then be used to provide sticky ends for ligation of additional segments. Alternatively, the tail may be complementary to a different segment of DNA, resulting in an amplified DNA wherein the segments are stitched together.

This additional feature of the invention is particularly applicable when it is desired to utilize as the purified defined DNA region only the exon portions (or other selected portions) of a long stretch of DNA. For example, the gene associated with cystic fibrosis (further discussed below) is about 250 kb in length and contains 27 exons which result in a messenger RNA of only about 6.1 kb. The 27 exons vary in size from 38 to 724 bp, Zielenski, J., et al. *Genomics* (1991) 1:214–228, all of them within a range suitable for application of the LSSP-PCR technique of the invention. If the LSSP-PCR technique is used to find a mutation anywhere in an exon region of the gene, all 27 exons would have to be amplified and independently subjected to the procedure in order to obtain their characteristic signatures. In order to apply the invention method to the cystic fibrosis gene, then, theoretically 27 separate determinations might be required, but for the following modification.

A single sample representing all 27 exons which can yield a characteristic LSSP-PCR signature can be prepared as follows. Upper and lower primers are provided for each of the 27 exons. One of the primers (all of the upper primers or all of the lower primers or some of each) has, in addition to the sequence complementary to the exon in question, a "tail" the sequence of which is shared with the tail of all other tailed primers for the exons. For example, if it is the upper primer that is provided with a tail, the sequence at the 3' end of the primer will be complementary to the exon target and the 5' portion will be the sequence common to all of the tails. The genomic sequence is then amplified, providing a mixture of all 27 exons, but all segments thus obtained will share the common sequence provided by the tail. The primer then used in the subsequent LSSP-PCR determination on the mixture will be complementary to the tail sequence. The signature that is then obtained according to the invention method will characterize this mixture of the 27 exons.

Application of the foregoing method, which might be called "primer tailing" can clearly be done in a variety of ways. For example, each exon could be amplified in a separate reaction or groups of exons in any arbitrary number per group can be amplified in a single PCR protocol. Only specific preferred exons which are most likely to contain mutations might be amplified. In addition, the general concept utilized in exon primer tailing can be employed not just for providing segments which are representative of exons, but for providing reaction mixtures which contain a multiplicity of purified forms of any defined DNA segments all of which will share a common tail sequence to which the primer used in the LSSP-PCR reaction can be specifically hybridized. The tails containing the extra common DNA sequence typically extend the primers in the direction which is not intended to be amplified in the PCR sequence.

It should be noted that the LSSP-PCR technique of the invention can be automated by providing suitable instrumentation. For example, the commercially available Beckman robot BIOTEK can be modified to automate this technique.

The patterns obtained using the LSSP-PCR technique of the invention are useful in various contexts. For example, the signatures obtained are useful in genetic counseling and diagnosis of genetically related diseases. Certain breast and ovarian cancers are characterized by typical alleles at the BCRA1 locus that has been identified and mapped to chromosome 17. Hall, J. M. et al. *Science* (1990) 250:1684–1689. It is estimated that certain alleles at this locus are responsible for as many as 15% of all breast cancers, and that a woman carrying a predisposition allele has a lifetime risk of 85% of developing this condition. Similarly, a locus predisposing to human colorectal cancer has been identified by Peltomaki, P. et al. *Science* (1993) 260:8–10. This locus is believed to account for a substantial percentage of colorectal cancer.

In cases such as the above, blood samples can be obtained as a source of genomic DNA from subjects to be tested and the relevant region amplified using a preliminary PCR reaction. The amplified defined locus is then subjected to the invention LSSP-PCR method. The resulting signature characteristic of the nucleotide sequence is compared to those for the normal and predisposition alleles to provide a prognosis for the subject of being affected by this disease. Other genes for which disease related alleles are known include the locus associated with cystic fibrosis, the gene that encodes steroid 21-hydroxylase and the locus associated with β-thalassemia. In addition, systemic mutations in cancer suppressor genes or in oncogenes, such as the P53 gene involving colon cancer and several other malignancies, will have both prognostic and diagnostic importance.

The locus associated with cystic fibrosis is of particular importance. Cystic fibrosis is an autosomal recessive disease with a frequency of 1 in 2000 caucasian newborns. This implies that about one in about every 22 caucasians is a carrier. After identification of the relevant locus, cystic fibrosis transmembrane conductance regulator (CFTR), it became clear that a small number of alleles were responsible for the disease in a majority of cases. Among these, the allele ΔF508 constitutes about 70% of all CFTR mutant alleles in the U.S. and Canada. Among Ashkenazi Jews, the W1282X allele accounts for 60% of the allelic mutants. These observations lead to the conclusion that by testing for a relatively small number of alleles, one could detect the majority of carriers in a population. It is estimated that testing for only 10 of the 27 alleles, 90–95% of the carriers could be identified and carrier screening is already done is some medical centers in the U.S. The remaining alleles, however, are distributed in more than 300 types and can only be included in the testing by DNA sequencing.

The technique of the present invention is, of course, applicable for a primary screening of CFTR alleles. If only a limited number of alleles need be tested, alternative techniques such as allele-specific hybridization could also be used. The LSSP-PCR technique of the invention is especially helpful, however, if all of the alleles need to be tested for. The exon primer tailing method, as described above, is particularly appropriate. This might be selectively applied to include in the assay only "hot" exons which are known in the case of CFTR to be exons 10, 11, 17B and 19. Alternatively, these, in addition to other exons or segments representing all of the exons, can be used in the single determination to obtain a characteristic signature.

This method might be particularly important, also, in a "second tier" test which might be provided subsequent to the screens now in use designed to pick up 90–95% of the carriers. For example, if one spouse tests positive in the "90%" screen and the other tests negative, the partner testing negative may want to verify that he or she is not a carrier of one of the alleles not tested for. The method of the invention would provide that option.

The LSSP-PCR method of the invention is particularly useful in detecting "private" mutations which are characteristic only of particular family lines in heritable diseases since these patterns are generally more complex and unpredictable in advance.

The method of the invention is also useful in diagnosing diseases which are characterized by particular infectious agents the presence of which could be verified by characteristic signatures of particular regions of their DNA. While standard PCR can in theory be used to indicate the presence or absence of a specific infectious agent (amplified DNA is present when the suspected infectious agent is present and absent when it is not), the methods of the invention offer valuable confirmation when a positive result is obtained. Furthermore, the invention method can be used to identify particular strains of infectious agents which might collectively be amplified in standard PCR by proper choice of primers. Also, in some instances, the particular variant present may indicate the course of a disease, as is the case with human papilloma virus. In addition, the acquisition of drug resistance in such agents through mutations in their DNA could be assessed using the same approach. It is known, for example, that resistance to AZT is indicated by certain mutations in the reverse transcriptase gene with the human immunodeficiency virus.

Thus, for use in diagnosis, prognosis, and genetic counseling, it is necessary only to ascertain a relevant region of the DNA as a purified DNA segment and to determine the patterns associated with the normal and mutated forms of the relevant region. A purified defined segment can then be used as a basis for obtaining the signature according to the method of the invention and for comparison to the normal and mutant standards.

The invention method can also be used for identification of individuals for forensic purposes (matching signatures of segments obtained and purified from DNA associated with the crime with that of the suspect) and ascertaining identity from familial relationships, for example, using mitochondrial DNA where identification is in doubt. This application is particularly relevant to identifying victims of disasters or to verify biological heritage, particularly through maternal inheritance.

Thus, the invention method has a wide variety of applications and is useful whenever it is desired to identify a particular individual, the relationship of that individual to others, or the status of the individual with respect to propensity to certain inherited diseases or the presence of disease states.

The following examples are intended to illustrate but not to limit the invention.

EXAMPLE 1

Detection of a Single Mutation in a 569 bp Fragment

Figure 1A:
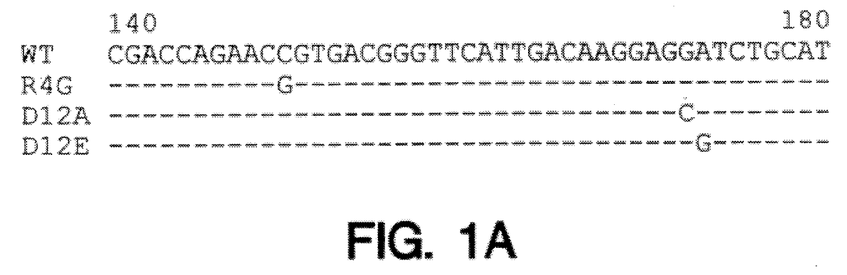
FIG. 1A shows the nucleotide sequence of a portion of the 569 bp DNA region of chicken smooth muscle myosin light chain between positions 140 and 180. The native sequence and 3 single base mutants (SEQ ID NO: 1, SEQ ID NO: 2, SEQ ID NO: 3 and SEQ ID NO:4) are shown.

569bp cDNA A encoding chicken smooth muscle myosin light chaining was subjected to mutagenesis using standard techniques. (Reinach, F. C., et al., *Nature* (1986) 322:80–83). The native and mutant inserts were removed from the pT7 plasmid vector in which they were cloned by cleavage with BamHI and EcoRI and purified by electrophoresis in low-melting point agarose. FIG. 1A shows the nucleotide sequences of the four inserts.

Fingerprints were produced by LSSP-PCR using 120 pmoles (4.8 µM) of primer 5'-TTCGCTATGTTCGAC-CAGTCA-3' (SEQ ID NO:5) which represents nucleotides 82 to 102 of the cDNA, 200 µM dNTPs, 4.0 units (160 U/ml) of Taq polymerase (Cenbiot, Rio Grande do Sul, Brazil), 10 mM Tris-HCl pH 8.6, 50 mM KCl, 1.5 mM $MgCl_2$, 0.001% gelatin, and approximately 15 pg of DNA in 25 µl reactions. Amplification was achieved using 35 repetitions of a two phase cycle consisting of one minute at 94° C. and one minute at 30° C. In the initial cycle the denaturation was prolonged for five minutes.

Figure 1B:
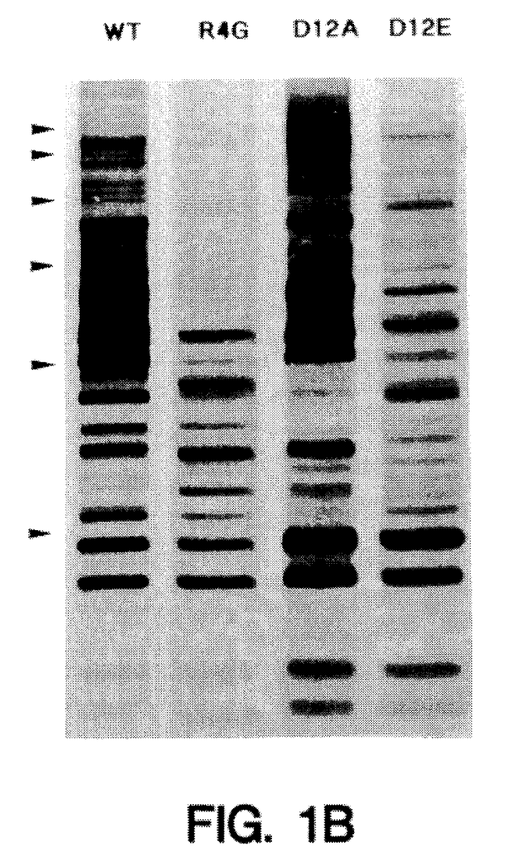
FIGS. 1B, 1C and 1D represent fingerprints obtained from the myosin light chain encoding DNA region for the wildtype and mutant DNAs represented in FIG. 1A.

Fifteen µl of each reaction were analyzed by electrophoresis. FIG. 1B shows an 8% polyacrylamide gel stained with silver salts (Santos, F. R., et al., *Hum Genet* (1993) 90:655–656). As seen, the wildtype and 3 mutants, R4G, D12A and D12E provide clearly distinctive fingerprints. This is true among the mutants whether the mutations are proximate or distal. (R4G v. D12A compared to D12A v. D12E).

Figure 1C:
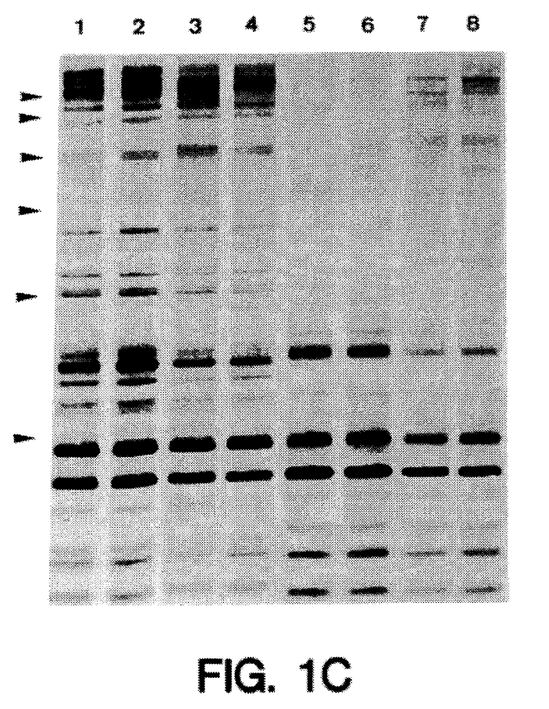

FIG. 1C is an 8% silver-stained polyacrylamide gel with duplicate fingerprints derived from RG4 and D12A obtained with different concentrations of the 569bp cDNA template. The conditions were as described above except that the final PCR reaction volume was 10 µl. As shown in FIG. 1C, lanes 1 and 2 are 70 pg of D12A; Lanes 3 and 4–14 pg of D12A; Lanes 5 and 6=36 pg of R4G; Lanes 7 and 8=7.3 pg of R4G. Five µl of the reaction products were loaded in each lane. As shown, the patterns are reproducible and do not change qualitatively when the concentration of the 569 bp template is altered.

Figure 1D:
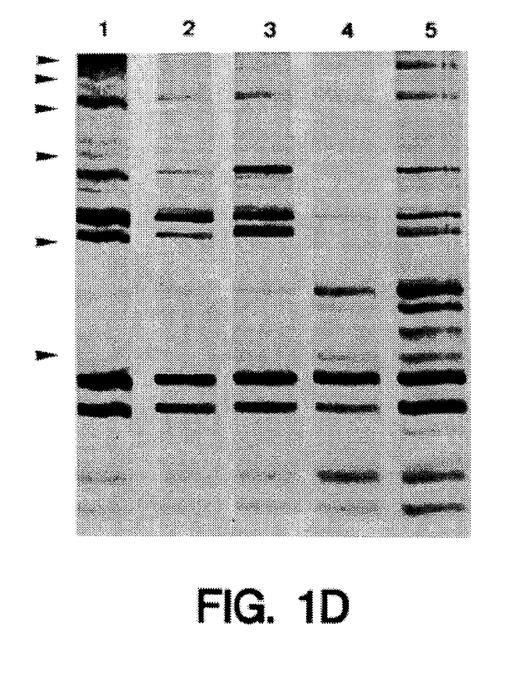

FIG. 1D shows LSSP-PCR fingerprints of mutant D12A produced on different days with different template concentrations. Lanes 1 and 2=10 pg; Lanes 3=20 pg; Lanes 4 and 5=100 pg. The volume loaded per lane was 7.5 µl in lanes 1 and 5 and 5.0 µl in the remaining lanes. FIG. 1D shows that the qualitative aspects of the pattern are indeed reproducible.

Thus, the defined DNA represented by the insert gives a characteristic fingerprint which is perceptibly altered by even a single mutation; the fingerprints can be obtained reproducibly.

(The arrows on the left of FIGS. 1B–1D represent the positions of the 123-bp ladder size standards, from bottom to top, 123, 246, 369,492, 611 and 738 base pairs respectively.)

EXAMPLE 2

Genetic Analysis of an Inherited Mutation

A family with X-linked dominant nephrogenic diabetes insipidus was used as subjects. This inherited disease is caused by defects in the vasopressin (V2) receptor gene, as described by Rosenthal, W., et al. *Nature* (1992)

359:233–235; van den Ouweland, A. M. W., et al. *Natural Genetics* (1992) 2:99–102; Pan, Y., et al. (*ibid.*) 103–106.

To obtain the defined DNA region, a 649 bp fragment of exon 2 of the gene was first amplified by PCR. Previous sequencing had shown that this fragment contained a single base change in nucleotide 839 of the cDNA sequence (wherein $A_{839}$ was converted to G leading to a $Tyr_{280}$ to Cys substitution).

100 ng of purified genomic DNA of the proband (P), his mother (M) and his father (F) were amplified by 35 cycles of PCR. The specific annealing temperature used was 64° C. for 1 min and the denaturation and extension temperatures were respectively 94° C. and 72° C. The primers used were NDI-1: 5'TCTGCAGATGGTGGGCATGT-3'(SEQ ID NO:6) and NDI-2: 5'-CTAGGTTGGGTTCAGGATG-3'(SEQ ID NO:7). The PCR conditions were as follows: each 20 µM dNTPs, 10 mM Tris HCl pH 8.6, 50 mM KCl, 1.5 mM $MgCl_2$, 0.001% gelatin and 20 pmoles of each primer. Fifteen µl of reaction product were run on an 1% low melting point agarose gel, stained with ethidium bromide and the specific amplified band was cut out.

Figure 2:
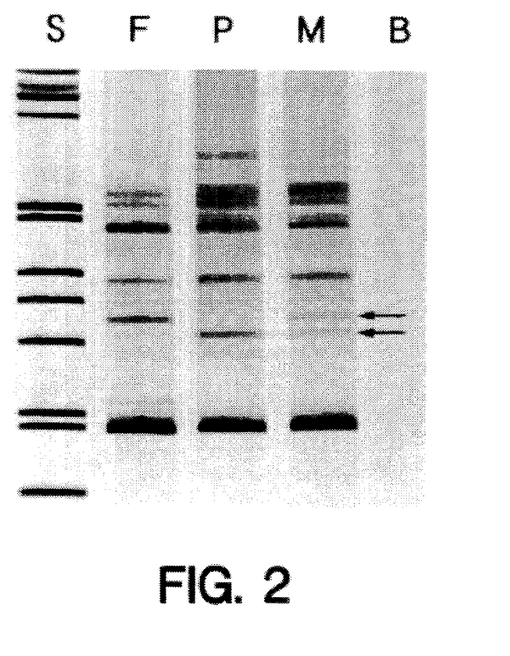
FIG. 2 shows fingerprints obtained from defined regions of the vasopressin (V2) genes of members of a family having a member afflicted with nephrogenic diabetes insipidus.

Samples of approximately 15 ng of the isolated bands were then subjected to a second round of PCR using only primer NDI-2, with the LSSP-PCR protocol described in Example 1 to produce the fingerprints shown in FIG. 2. FIG. 2 shows a silver-stained 8% polyacrylamide gel produced by amplifying the gene for the vasopressin V2 receptor from the proband (P) who presented with nephrogenic diabetes insipidus and who had a family history of the disease segregating in a characteristic X-linked recessive fashion and his carrier mother (M) and normal father (F). The lane labeled S shows molecular size standards, from bottom up, 154, 203,220, 298, 344, 396, 506, 517, 1018, 1636 and 2056 base pairs respectively and lane B corresponds to the blank control without DNA.

The proband and father each have a single copy of the gene. Although the genes differ by only base substitution, the fingerprints as shown in FIG. 2 are clearly different. The major distinction in this instances resided in a prominent band of about 310 bp (arrowed in the figure). The mother is heterozygous for the mutation and thus has both of the bands that distinguish father and son. Thus, the fingerprints distinguished an unaffected hemizygous individual, an affected hemizygous individual, and a heterozygote.

EXAMPLE 3

Identification of Individuals using Mitochondrial DNA

The control (D-loop) region of human mitochondrial DNA is known to differ from between 1 to 15 bases between unrelated individuals (Vigilant, L., et al. *Proc Natl Acad Sci U.S.A.*, (1989) 86:9350–9354; Stoneking, M., et al. *Am J Hum Genet* (1991) 370–382; Horai, S., et al. *Phil Trans R Soc Lond* (1991) B 333:409–417; Ginther, C., et al. *Nature Genet* (1992) 2:135–138).

Total genomic DNA was isolated from peripheral blood by digestion with SDS-proteinase-K followed by phenol chloroform extraction and ethanol precipitation. The final concentration of DNA obtained was determined by agarose gel electrophoresis against known standards. The 1,024-bp region of the mtDNA control (D-loop) region was amplified from 200 ng of DNA using the primers L15996 and H408 both described by Vigilant, L., et al. (*supra*). The reaction mix consisted of 5 pmoles of each primer, 50 µM dNTPs, 1.5 mM $MgCl_2$, 50 mM KCl, 0.1% Triton X-100, 10 mM Tris-HCl and 0.25 units of Taq polymerase, pH 9.0 in a final volume of 25 µl. The reaction cycle consisted of denaturation at 94° C. for 45 seconds, annealing at 56° C. for 1 minute and extension at 74° C. for 1 minute. In the first cycle the denaturation was prolonged for 5 minutes. Ten µl of reaction products were run on an 0.8% low melting point agarose gel, stained with ethidium bromide and purified by excision from the gel.

A sample of the isolated bands of approximately 15 ng of DNA contained in agarose were then subjected to LSSP-PCR under the conditions described in Example 1 using 48 pmoles of primer L15996 in a 10 µl reaction volume. The reaction products were the run on a 6% polyacrylamide gel and stained with silver as described by Santos, F. R., et al. (*Hum Genet* (1993) 90:655–656).

Results from 24 unrelated individuals provided different mt DNA fingerprints (data not shown), while mother-child pairs were identical as expected (Giles, R. E., et al. *Proc Nat Acad Sci U.S.A.*, (1980) 77:6715–6719). The results from two mother-child pairs are shown in FIG. 3.

Figure 3:
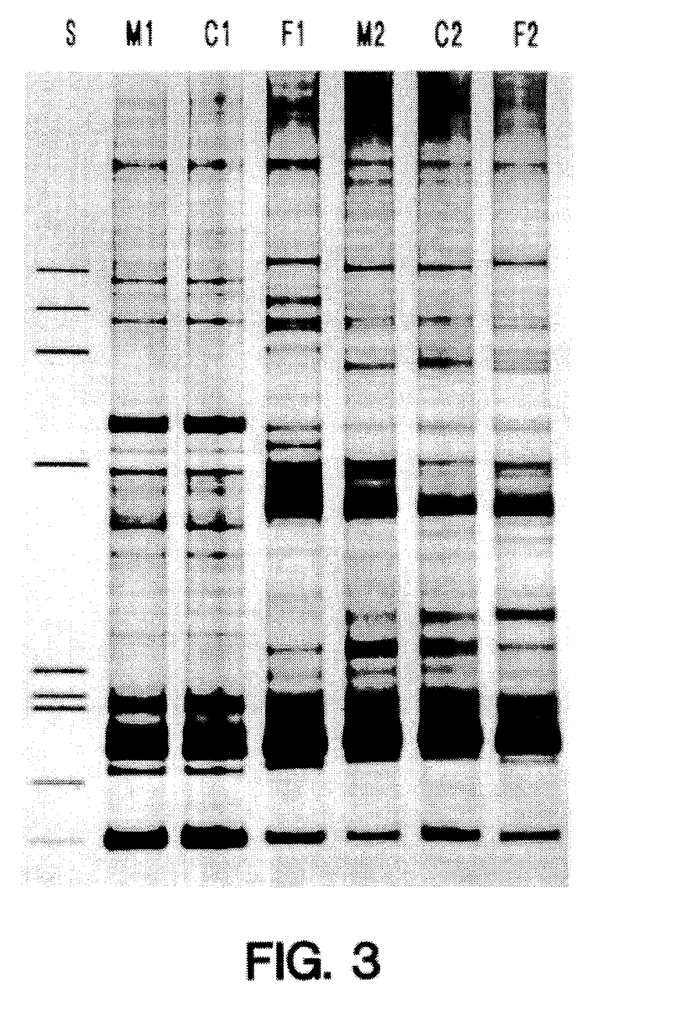
FIG. 3 shows fingerprints of the D-loops of mitochondrial DNA amplified as defined regions from mother, father and child in each of two families.

In FIG. 3, the bands on lane S are size standards with, from bottom up, 118, 194, 234, 271, 281, 310, 603, 872, 1078 and 1353 bp. In both families 1 and 2, M1 and C1 or M2 and C2 (mother and child) are identical while the pattern exhibited by the father (F1 or F2) is different. The F1 pattern clearly is more distinct from his family members than that of F2. In further studies, we have found a correspondence between the number of changes in the sequence and the extent of variation in the binding pattern; thus, it would appear that F2 has fewer sequence differences from M2 and C2 than does F1 from M1 and C1.

EXAMPLE 4

Comparison of Detection Methods

This example provides a comparison of the display of D-loop LSSP-PCR products resolved in silver stained polyacrylamide gels with results obtained in an automatic laser fluorescence (ALF Pharmacia) sequencer. The mtDNA from M1, C1 and F1 of Example 3 was amplified and purified exactly as described in Example 3. The amplified product was subjected to LSSP-PCR using primer L15996 labeled with fluorescence as described in Example 1 except that the reaction volume was increased to 25 µl. Following the reaction, 10 µl were run on a 6% polyacrylamide gel and stained with silver and 5 µl were analyzed in the automated sequencer using a six hour runs on a denaturing 6% urea polyacrylamide gel using the default conditions in the ALF. A comparison of the results displayed in these two different manners is shown in FIG. 4.

Figure 4A:
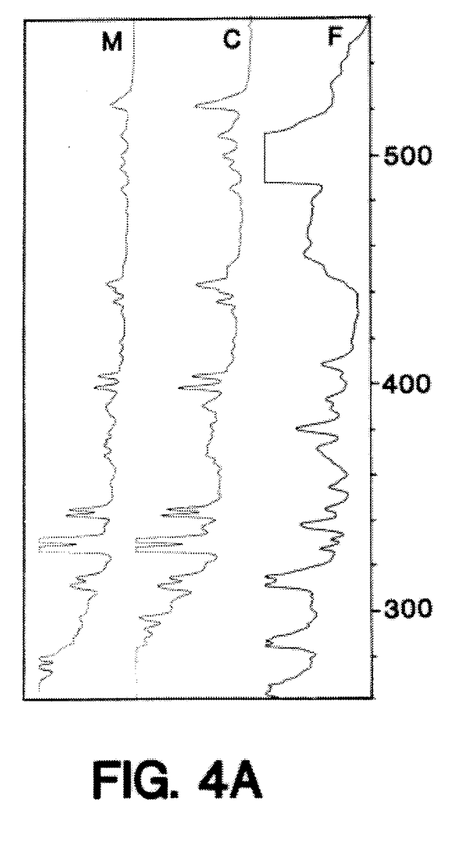
FIG. 4A shows the results obtained in an automatic laser fluorescence sequencer.
Figure 4B:
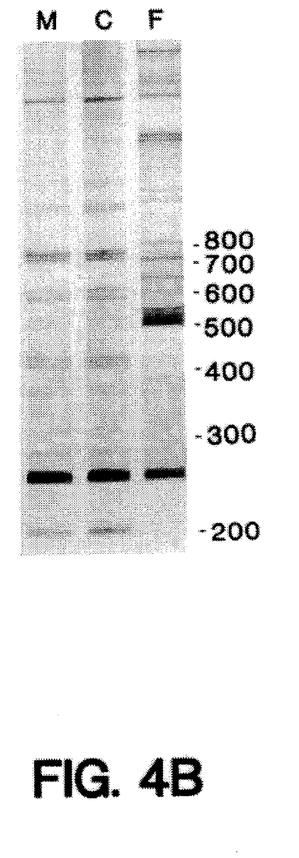
FIG. 4B shows results on the same samples obtained using a silver stained gel.

FIG. 4A shows the results of analysis in the automated sequencer; FIG. 4B shows the results on silver stained gels as described above. The molecular size range covered by the fluorescent run is more restricted (250–550 bp) than that of silver stained gel (200>2000 bp) but the resolution is superior. Again, the identity of M and C as opposed to F is clearly evident. (The values on the right indicate size values in base pairs calculated from molecular weight standards.)

EXAMPLE 5

Effect of Segment Length and Positioning of the Single Primer

A segment obtained by standard PCR techniques of D-loop mitochondrial DNA as described in the previous examples was prepared as a series of segments of varying lengths. Total genomic DNA was isolated from peripheral blood by digestion with SDS-proteinase K follwed by phenol chloroform extraction and ethanol precipitation. The final concentration of DNA obtained was determined by agarose gel electrophoresis against known standards. Increasing sizes of the mtDNA control region were then amplified from 200 ng of DNA using the following primers and 0.25 units of Taq polymerase.

L15926: 5'-TCAAAGCTTACACCAGTCTTG-TAAACC-3'(SEQ ID NO:8)

L15996: 5'-CTCCACCATTAGCACCCAAAGC-3'(SEQ ID NO:9)

H16197: 5'-TGATTGCTGTACTTGCTTGTAAG-3'(SEQ ID NO:10)

H16277: 5'-CACCCCTCACCCACTAGGATA-3'(SEQ ID NO:11)

H16347: 5'-ATGGGGACGAGAAGGGATTTGA-3'(SEQ ID NO:12)

H16401: 5'-TGATTTCACGGAGGATGGTG-3'(SEQ ID NO:13)

H16498: 5'-CCTGAAGTAGGAACCAGATG-3'(SEQ ID NO:14)

H408: 5'-CTGTTAAAAGTGCATACCGCCA-3'(SEQ ID NO:15)

H580: 5'-TTGAGGAGGTAAGCTACATA-3'(SEQ ID NO:16)

The reaction mix consisted of 5 pmoles of each primer, 50 µM dNTPs, 1.5 mM $MgCl_2$, 50 mM KCl, 0.1% Triton X-100 and 10 mM Tris-HCl, pH 9.0 in a final volume of 25 µl. The reaction cycle consisted of denaturation at 94° C. for 45 seconds annealing at 56° C. for 1 minute and extension at 74° C. for 1 minute. In the first cycle the denaturation was prolonged for 5 minutes.

Ten µl of reaction product were run on a 0.8% low melting point agarose gel, stained with ethidium bromide and purified by excision from the gel. A sample of the isolated bands of approximately 15 ng of DNA contained in agarose were then subjected to LSSP-PCR under the conditions described in the previous Examples using 48 pmoles of primer L15996 in a 10 µl reaction volume. The reaction products were then run on a 6% polyacrylamide gel and stained with silver as described above.

Figure 5:
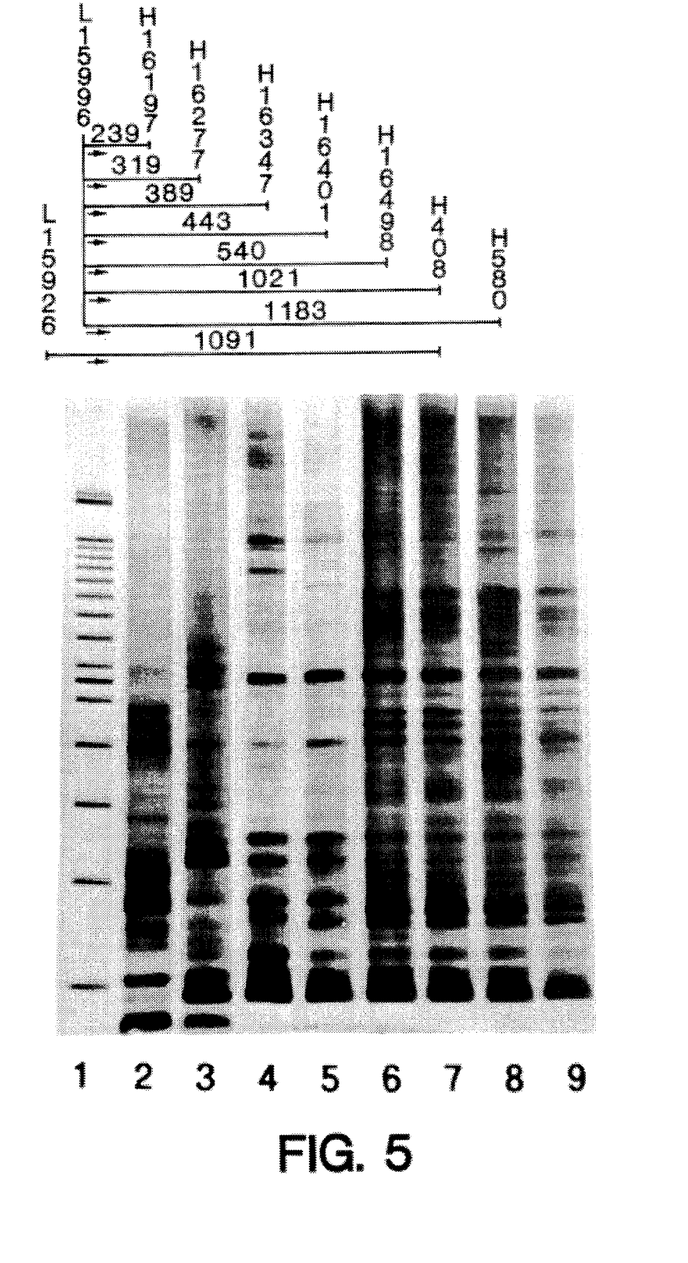
FIG. 5 shows the effect of the length of DNA segment subjected to LSSP-PCR on the resulting signature.

The results are shown in FIG. 5. The bands on the leftmost lane are 100 bp-ladder size standards, starting with, from bottom up, 200 bp. As shown in FIG. 5, the segments subjected to LSSP-PCR were complementary at one extremity to a single primer and extended to various lengths ranging from 239 bp to 1183 bp. An additional fragment was obtained containing a total of 1091 bp wherein 1021 bp represented a sequence identical to a 1021 bp fragment as described above and 70 bp extended in the other direction from the location of the primer.

As FIG. 5 shows, lanes 2 and 3, which represent the results from the 239 bp and 319 bp fragments respectively, do not provide identical patterns with each other or with the pattern obtained in lane 4 which represents the results from the fragment of 389 bp. However, the results obtained in lanes 5–9, which represent results from fragments of 443 bp–1183 bp as well as the 1091 bp fragment described above, give substantially similar patterns. Thus, maximum information relative to the amount of sequence provided can be obtained from fragments less than about 550 bp. This does not imply that single base changes cannot be identified in longer fragments; this merely implies that the sensitivity of the assay can be improved by multiple determinations on segments of longer length.

---

We claim:

1. A method to obtain a signature characteristic of the nucleotide sequence of a purified cloned or amplified defined DNA segment which method consists essentially of:

subjecting said segment to multiply cycles of replication in the presence of a single primer fully complementary to a portion of at least about ten nucleotides of said segment, wherein said portion is not a repetitive sequence or part of a gene cluster within said DNA segment under conditions of low stringency at 25° C.–40° C. a primer concentration in the range of 2–10 µM, and a polymerase concentration in the range of 60–200 units/ml to obtain a mixture of replicated DNA molecules which result from said multiplicity of low stringency cycles of replication; and determining the size of the replicated DNA molecules in the mixture thus obtaining a signature characteristic of said nucleotide sequence.

2. The method of claim 1 wherein said determining is conducted by subjecting the mixture to gel electrophoresis to separate the replicated DNA molecules into separate bands.

3. The method of claim 1 wherein said DNA segment is obtained by a method comprising selectively amplifying a region of genomic or mitochondrial DNA or cloning said DNA segment.

4. The method of claim 1 wherein said DNA segment is obtained from the cystic fibrosis transmembrane conductance regulator locus.

5. The method of claim 1 wherein said DNA segment is obtained from the DNA associated with the BCRA1 locus.

6. The method of claim 1 wherein said DNA segment is obtained from mitochondrial DNA.

7. A signature characteristic of a defined DNA segment which signature consists essentially of a developed chromatographic or electrophoretic support obtained by chromatography or electrophoresis of a mixture wherein said mixture is obtained by a process consisting essentially of subjecting said DNA segment to multiple cycles of replication in the presence of a single primer fully complementary to a portion consisting of at least about 10 nucleotides of said segment, wherein said portion is not a repetitive sequence or part of a gene cluster within said DNA segment, under conditions of low stringency at 25° C.–40° C., a primer concentration in the range of 2–10 µM, and a polymerase concentration in the range of 60–200 units/ml.

8. A method to obtain a signature characteristic of the nucleotide sequence of at least two different DNA segments which method comprises amplifying regions representing each of said at least two DNA segments from duplex DNA in a standard polymerase chain reaction (PCR) conducted in the presence of primers complementary to the opposing strands of said duplex at opposite extremities of each said DNA region, wherein one of the primers in the PCR of each region is extended at its 5' end by a DNA sequence tail common to primers for each region to obtain said at least two different DNA segments in purified and amplified form, followed by a process that consists essentially of subjecting each segment to multiple cycles of replication in the presence of a single primer fully complementary to a portion consisting of at least about 10 nucleotides of said tail, wherein said portion is not a repetitive sequence or part of a gene cluster within said DNA segment under conditions of low stringency at 25° C.–40° C., a primer concentration in the range of 2–10 µM, and a polymerase concentration in the range of 60–200 units/ml to obtain a mixture of replicated DNA molecules which result from said multiplicity of low stringency cycles of replication; and determining the size of the replication DNA molecules in the mixture.

9. A method to determining the presence or absence of an allele predisposing a subject to a disease or condition which method comprises:

obtaining genomic DNA from said subjects;

providing, in a purified and amplified or cloned form, a DNA segment representing a defined region of said genomic DNA from the locus of the allele; followed by a process consisting essentially of subjecting said segment to multiple cycles of replication in the presence of a single primer fully complementary to a portion consisting of at least about ten nucleotides of said segment, wherein said portion is not a repetitive sequence or part of a gene cluster within said DNA segment under conditions of low stringency at 25° C.–40° C., a primer concentration in the range of 2–10 µM, and a polymerase concentration in the range of 60–200 units/ml to obtain a mixture of replicated DNA molecules which result from said multiplicity of low stringency cycles of replication; and determining the sizes of the replicated DNA molecules in the mixture thus obtaining a signature characteristic of said locus comparing said determining signature with the signature of the mixture produced and determined in an analogous manner from the allele whereby an identity of said signatures indicates the presence of the allele and nonidentity of the signatures indicates the absence of the allele.

10. A method to determined the presence or absence of an infectious agent in a biological sample which method comprises:

subjecting said sample to the polymerase chain reaction using primers characteristics of the suspected infectious agent and purifying the reaction product to obtain a purified DNA segment;

subjecting said segment to replication in a process consisting essentially of multiple cycles of replication in the presence of a single primer fully complementary to a portion consisting of at least about ten nucleotides of said segment, wherein said portion is not a repetitive sequence or part of a gene cluster within said DNA segment, under conditions of low stringency at 25° C.–40° C., a primer concentration in the range of 2–10 µM, and a polymerase concentration in the range of 60–200 units/ml to obtain a mixture of replicated DNA molecules which result from said multiplicity of low stringency cycles of replication; and determining the sizes of the replicated DNA molecules in the mixture thus obtaining a signature characteristic of said segment comparing said determining signature with the signature of the mixture produced and determined in an analogous manner from the suspected infectious agent;

wherein identity of the signature indicates the presence of said infectious agent.

11. A method to determine the relationship of a subject through the maternal line to another individual which method comprises:

obtaining mitochondrial DNA from said subject and from said other individual;

obtaining in purified and cloned or amplified form DNA segments representing a defined region of the mitochondrial DNA of the subject and of said individual; followed by a process consisting essentially of subjecting each segment to multiple cycles of replication in the presence of a single primer fully complementary to a portion consisting of at least about ten nucleotides of each said segment, wherein said portion is not a repetitive sequence or part of a gene cluster within said DNA segment, under conditions of low stringency at 25° C.–40° C., a primer concentration in the range of 2–10 µM, and a polymerase concentration in the range of 60–200 units/ml to obtain a mixture of replicated DNA molecules which result from said multiplicity of low stringency cycles of replication; and determining the sizes of the replicated DNA molecules in each said mixture thus obtaining a signature characteristic of each segment, and comparing the signature of the mixture obtained from the subject with the signature of the mixture obtained from the other individual;

whereby identity of said signatures indicates relationship of the subject with the other individual through the maternal line.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 43 base pairs
( B ) TYPE: nucleic acid
( C ) STRANDEDNESS: single
( D ) TOPOLOGY: linear ( x i ) SEQUENCE DESCRIPTION: SEQ ID NO:1:

CGACCAGAAC CGTGACGGGT TCATTGACAA GGAGGATCTG CAT                     43

( 2 ) INFORMATION FOR SEQ ID NO:2:

( i ) SEQUENCE CHARACTERISTICS:
( A ) LENGTH: 43 base pairs
( B ) TYPE: nucleic acid
( C ) STRANDEDNESS: single
( D ) TOPOLOGY: linear ( x i ) SEQUENCE DESCRIPTION: SEQ ID NO:2:

CGACCAGAAC GGTGACGGGT TCATTGACAA GGAGGATCTG CAT                     43

( 2 ) INFORMATION FOR SEQ ID NO:3:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:3:

```
CGACCAGAAC CGTGACGGGT TCATTGACAA GGAGCATCTG CAT                    43
```

( 2 ) INFORMATION FOR SEQ ID NO:4:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:4:

```
CGACCAGAAC CGTGACGGGT TCATTGACAA GGAGGGTCTG CAT                    43
```

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:5:

```
TTCGCTATGT TCGACCAGTC A                                            21
```

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:6:

```
TCTGCAGATG GTGGGCATGT                                              20
```

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:7:

```
CTAGGTTGGG TTCAGGATG                                               19
```

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:8:

```
TCAAAGCTTA CACCAGTCTT GTAAACC                                      27
```

( 2 ) INFORMATION FOR SEQ ID NO:9:

( i ) SEQUENCE CHARACTERISTICS:
        ( A ) LENGTH: 22 base pairs ( B ) TYPE: nucleic acid
( C ) STRANDEDNESS: single
( D ) TOPOLOGY: linear ( x i ) SEQUENCE DESCRIPTION: SEQ ID NO:9:

CTCCACCATT AGCACCCAAA GC                22

( 2 ) INFORMATION FOR SEQ ID NO:10:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:10:

TGATTGCTGT ACTTGCTTGT AAG               23

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:11:

CACCCCTCAC CCACTAGGAT A                 21

( 2 ) INFORMATION FOR SEQ ID NO:12:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:12:

ATGGGGACGA GAAGGGATTT GA                22

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:13:

TGATTTCACG GAGGATGGTG                   20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:14:

CCTGAAGTAG GAACCAGATG                   20

( 2 ) INFORMATION FOR SEQ ID NO:15:

( i ) SEQUENCE CHARACTERISTICS:
        ( A ) LENGTH: 22 base pairs
        ( B ) TYPE: nucleic acid
        ( C ) STRANDEDNESS: single ( D ) TOPOLOGY: linear ( x i ) SEQUENCE DESCRIPTION: SEQ ID NO:15:

CTGTTAAAAG TGCATACCGC CA 22

( 2 ) INFORMATION FOR SEQ ID NO:16:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:16:

TTGAGGAGGT AAGCTACATA 20